(12) United States Patent
Rasche et al.

(10) Patent No.: US 6,959,067 B2
(45) Date of Patent: Oct. 25, 2005

(54) X-RAY IMAGING METHOD AND A 3D-ROTATIONAL X-RAY APPARATUS FOR APPLYING THIS METHOD

(75) Inventors: Volker Rasche, Hamburg (DE); Steffen Weiss, Hamburg (DE); Johannes Catharina Antonius Op De Beek, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 222 days.

(21) Appl. No.: 10/022,383

(22) Filed: Oct. 30, 2001

(65) Prior Publication Data

US 2002/0126794 A1 Sep. 12, 2002

(30) Foreign Application Priority Data

Nov. 2, 2000 (EP) .............................. 00203825

(51) Int. Cl.[7] .................................. A61B 6/00
(52) U.S. Cl. .............................. 378/8; 378/62; 600/428
(58) Field of Search .............................. 378/8, 15, 62, 378/95, 901; 382/130, 131; 600/425, 428

(56) References Cited

U.S. PATENT DOCUMENTS 5,852,646 A * 12/1998 Klotz et al. ................. 378/8
6,079,876 A * 6/2000 Schuetz ..................... 378/205
6,120,180 A * 9/2000 Graumann .................. 378/206
6,266,553 B1 * 7/2001 Fluhrer et al. .............. 600/428
6,324,254 B1 * 11/2001 Pflaum ....................... 378/95

FOREIGN PATENT DOCUMENTS

| DE | 19853964 C | 5/2000 | ............ A61B/6/03 |
| JP | 6-319284 | 11/1994 | |
| JP | 11-332273 | 11/1999 | |
| JP | 2000-341985 | 12/2000 | |

OTHER PUBLICATIONS

McKinnon et al.: "Towards imaging the beating heart usefully with a conventional CT scanner," IEEE Transactions On Biomedical Engineering, IEEE Inc. New York, US, vol. EME–28, No. 2, Feb. 1981, pp. 123–127.

* cited by examiner

*Primary Examiner*—Edward J. Glick
*Assistant Examiner*—Courtney Thomas
(74) *Attorney, Agent, or Firm*—John Vodopia

(57) ABSTRACT

An X-ray imaging method comprises forming 2-dimensional X-ray images of an object to be examined, for example the coronary vascular system of a patient, and reconstruction of a 3-dimensional volume thereof. With a relatively long run length of a scan rotation over substantially 180° of at least 15 sec. and preferably about 20 sec. A sufficient number of images is obtained to perform a more accurate volume reconstruction. This reconstruction method may be combined with existing modelling techniques.

5 Claims, 1 Drawing Sheet

X-RAY IMAGING METHOD AND A 3D-ROTATIONAL X-RAY APPARATUS FOR APPLYING THIS METHOD

FIELD OF THE INVENTION

The present invention relates to an X-ray imaging method comprising forming a set of 2-dimensional X-ray images of an object to be examined, for example the coronary vascular system of a patient, by means of a scan rotation of an X-ray source around said object over a run length, said X-ray images being acquired at predetermined characteristic time moments in cardiac cycle of the object and a reconstruction of a 3-dimensional volume thereof. The invention further relates to a 3D-rotational X-ray apparatus for applying this method, the apparatus comprising a circular C-arm with a drive, the C-arm accommodating an X-ray source and an X-ray image pick-up device and being rotatable over an angle of substantially 180° around its center, triggering means for triggering the X-ray images at predetermined characteristic time moments in the cardiac cycle of the object and means for processing the images obtained to reconstruct a 3-dimensional volume of the object.

BACKGROUND OF THE INVENTION

Such a method and apparatus are well known, e.g. from U.S. Pat. No. 5,852,646. In said document a 3-dimensional volume of an object can be derived from a number of 2-dimensional computer tomograms by means of a CT-apparatus. The obtained 3-dimensional volume is related to the X-ray images; an association of corresponding projection images of this volume with the X-ray images results in a series of superposition images, which reproduces the two anatomic structures in geometrically correct association. In such a way information, inherent to CT-measuring methods, e.g. information about tumors, is combined with typically X-ray information, e.g. information about blood vessels.

In general, a similar set of X-ray images can be obtained by using an X-ray apparatus with a rotatable source around its isocenter. To enable such rotations conventional X-ray apparata are equipped with a C-arm, the technical details of such a construction falling within the scope of general knowledge of a person skilled in the art of X-ray imaging. When a method as described in the opening paragraph is applied to a moving object, such as a beating heart or more specifically the coronary vascular system of a beating heart of a human or animal, filled with a contrast medium, it is often standard practice to use a C-arm rotation speed in the X-ray apparatus of about 30°/s (degrees per second) or a scan duration or run length of about 6 s. During each run images are obtained for only certain angle areas. To cover the whole angle area of 180° several runs are necessary, the starting angle of each run relative to the cardiac cycle being adjusted by triggering the start of the run with a certain phase within the cardiac cycle. The images obtained can be used for a reconstruction of a 3-dimensional volume. During this process a movement of the heart contributes to artefacts in the reconstructed image. With a heart rate of 60 beats per minute and a framerate of for example 25 images per second during a scan movement over 180°, during each hart beat 25 images are obtained and with 5 images in each specific phase of the cardiac cycle, 6 times 5 images are obtained, or, in other words, during each scan 5 times 6 corresponding X-ray images of a quasi-stationary heart can be obtained, which can be used for reconstruction of a 3-dimensional volume.

Problems of the known method are the necessity to correlate the different sub-runs in order to produce the 180° run as well as poor quality of the reconstructed image.

SUMMARY OF THE INVENTION

It is an object of the invention to provide a method where the above problems are solved. According to the invention, the method as described in the opening paragraph is characterized in that the run length of the scan rotation over substantially 180° is at least 15 s and preferably about 20 s. Contrary to the present tendency to increase the C-arm rotation speed, it has been found that the above method can be improved by a slower rotational scanning speed. With a run length of about 20 s, i.e. a C-arm rotation speed of substantially 10°/s, and with the above parameters, during each scan about 5 times 20 corresponding X-ray images of a quasi-stationary heart can be obtained. Thus, by reducing the speed of the rotation of the X-ray source around the object more X-ray images corresponding to the same phase in the cardiac cycle are acquired. This leads to reduced noise in the resulting reconstructed 3-dimentional volume.

A further embodiment of the X-ray imaging method according to the invention is characterized in that before reconstruction, images obtained at predetermined corresponding characteristic time moments in successive cardiac cycles are correlated with each other. This technical measure is based on the insight that each phase in the spectrum of cardiac activity in general represents the same spatial orientation and geometry of the heart muscle. Thus by correlating the X-ray images corresponding to the same phase of the cardiac activity, for example by known mathematical algorithms, one can further reduce noise in the final reconstruction of the 3-dimentional volume.

A further embodiment of the X-ray imaging method according to the invention is characterized in that the characteristic time moments substantially correspond to R-peaks of the cardiac cycle. This technical measure provides the possibility to acquire images of the quasi-stationary heart, when the cardiac muscle is relaxed, thus reducing the image reconstruction noise due to the movement of the cardiac muscle. The methods of ECG-triggering are known and present no technical difficulty for those skilled in the art.

A further embodiment of the X-ray imaging method according to the invention is characterized in that before a reconstruction, images obtained at neighbouring time moments in a predetermined characteristic time interval of a cardiac cycle are correlated with each other. This technical measure is based on the insight that if one determines a certain time interval around a characteristic moment in the ECG spectrum, for example around the R-peak, the movement of the heart muscle within this time interval has taken place to a such small degree that the X-ray images acquired within this predetermined time interval can be used for the image reconstruction. This technical measure provides the net noise reduction as the minor spatial movements or deformations of the heart muscle are compensated by the total number of the useful X-ray images contributing to the final dataset. Furthermore, it is still possible to correlate measurements at corresponding time moments of successive cardiac cycles with each other and, in case a reconstruction of a diminished quality is obtained, to combine the reconstruction with existing modelling techniques.

As already said, the invention also relates to a 3D-rotational X-ray apparatus for applying the above method. Such is an apparatus is already described in the opening paragraph and is, in accordance with the invention, further characterized in that the drive of the C-arm is adjusted to a run length of a scan rotation over substantially 180° which is at least 15 s and preferably about 20 s.

BRIEF DESCRIPTION OF THE DRAWINGS

These and other aspects of the invention will be apparent from and elucidated with reference to the drawing and the embodiment described hereinafter. In the drawing.

DETAILED DESCRIPTION OF THE PREFERRED EMBODIMENTS

Figure 1:
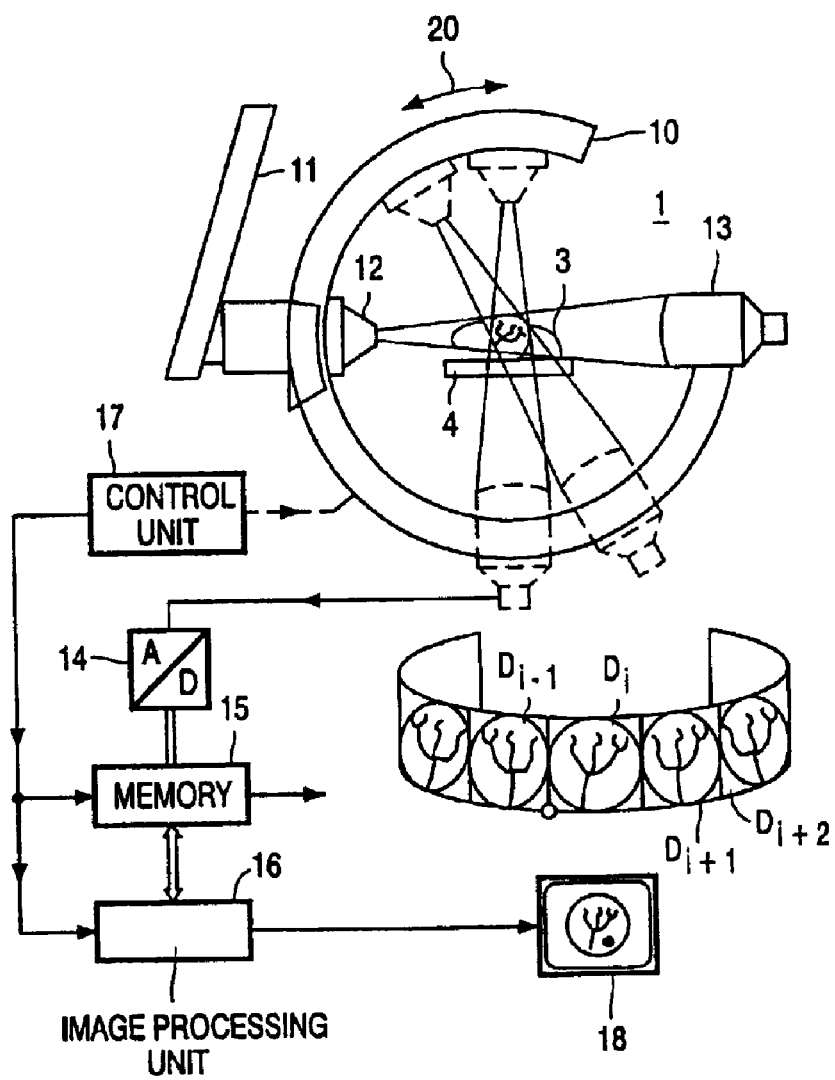
FIG. 1 shows diagrammatically an X-ray imaging apparatus, in which the method according to the invention can be applied.

The imaging apparatus of FIG. 1 serves to form two-dimensional X-ray images of an object to be examined, particularly a periodically moving object such as the heart and the coronary vascular system of the heart of a patient, from which two-dimensional images via reconstruction a 3-dimensional volume of the object can be obtained.

The imaging apparatus 1 includes a circular C-arm 10 which is mounted on a (only partly shown) stand 11. The C-arm can be rotated over an angle of for example 180° around its center in the direction of the double arrow 20 by means of a motor drive (not shown in the figure). The C-arm 10 accommodates an X-ray source 12 and an X-ray image pick-up device 13, which are aligned relative to each other in such a manner that an X-ray image can be formed of a volume to be examined around said center. A plurality of X-ray images can thus be formed. This plurality of X-ray images shows the volume to be examined from different angular positions (some of which are denoted by dashed lines) of the image-forming system 12, 13. The X-ray image pick-up device 13 may be an X-ray image intensifier whereto a television chain is connected whose output signals are digitized by an analogue-to-digital converter 14 and stored in a memory 15 so that the overall X-ray image series ( ... $D_{i-1}$, $D_i$, $D_{i+1}$, $D_{i+2}$, ... ) will have been stored at the end of the examination. These X-ray images can be processed by known reconstruction methods in an image processing unit 16 to obtain the 3-dimensional volume to be examined. This volume or projections or cross sections thereof can be displayed on a monitor 18. The various components of the imaging apparatus 1 are controlled by means of a control unit 17.

Figure 2:
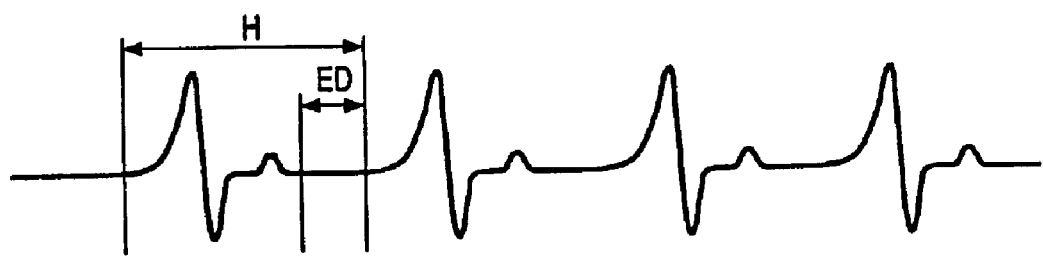
FIG. 2 shows a cardiac cycle and preferred data acquisition times.

FIG. 2 is a diagram showing the substantially periodic cardiac cycles H and preferred data acquisition time intervals during end diastole ED on an ECG scale. A heart is relatively stationary during the end diastole time interval.

According to the invention, the drive of the C-arm 10 is able or adjusted to perform a scan with a run length over 180° of at least 15 s and preferably about 20 s. With a heart rate of 60 beats per second and 25 images per second and a run length of about 20 s, i.e. a C-arm rotation speed of substantially 10°/s, during each scan about 5 times 20 corresponding non-moving X-ray images are obtained so that an improved reconstruction of the 3-dimensional volume will be possible.

The present invention is not restricted to the embodiment described with reference to the accompanying drawing, but also relates to modifications thereof as far as such modifications fall within the scope of the following claims. So, it is possible to reduce the number of measuring points in the end diastole time intervals or to reduce the number of corresponding measuring points in successive cardiac cycles. Although such a reduction results in a reconstruction of less quality, the negative effect thereof may be compensated by combination of the reconstruction method with existing modelling techniques. Of course, also in the preferred embodiment with a large number of measuring points in each diastole time interval, reconstruction may be combined with modelling techniques.

What is claimed is:

1. An X-ray imaging method comprising the steps of:
   forming a set of 2-dimensional X-ray images of a coronary vascular system of an object to be examined by means of a scan rotation of a single imaging device having an X-ray source and an X-ray pick-up device, around said object over a run length, said X-ray images being acquired at predetermined characteristic time moments in a cardiac cycle of the object; and
   reconstructing a 3-dimensional volume of the object from said set of 2-dimensional X-ray images, wherein the run length of the scan rotation over substantially 180° is approximately 10° per second such that approximately 100 X-ray images corresponding to a quasi-stationary heart are obtained during the scan rotation.

2. An X-ray imaging method according to claim 1, wherein, before the reconstructing step, images obtained at predetermined corresponding characteristic time moments in successive cardiac cycles are correlated with each other.

3. An X-ray imaging method according to claim 2, wherein the characteristic time moments substantially correspond to R-peaks of the cardiac cycle.

4. An X-ray imaging method according to claim 1, wherein, before the reconstructing step, images obtained at predetermined neighboring time moments in a predetermined characteristic time interval of a cardiac cycle are correlated with each other.

5. 3D-rotational X-ray apparatus, comprising a circular C-arm with a drive, the C-arm accommodating a single imaging device having an X-ray source and an X-ray pick-up device, and an X-ray image pick-up device and being rotatable over an angle of substantially 180° around its center by means of said drive, triggering means for triggering the X-ray images at predetermined characteristic time moments in a cardiac cycle of an object, and means for processing the images obtained to reconstruct a 3-dimensional volume of the object, wherein the drive of the C-arm is adjustable to a run length of a scan rotation over substantially 180° at approximately 10° per second such that approximately 100 X-ray images corresponding to a quasi-stationary heart are obtained during the scan rotation.

* * * * *